(12) United States Patent
Rzany et al.

(10) Patent No.: US 10,596,299 B2
(45) Date of Patent: Mar. 24, 2020

(54) METHOD FOR REDUCING PARAVALVULAR LEAKS WITH DECELLULARIZED TISSUE

(71) Applicant: BIOTRONIK AG, Buelach (CH)

(72) Inventors: Alexander Rzany, Nuremberg (DE); Wilhelm Erdbruegger, Constance (DE); Nina Lehenberger, Fuerth (DE)

(73) Assignee: Biotronik AG, Buelach (CH)

( * ) Notice: Subject to any disclaimer, the term of this patent is extended or adjusted under 35 U.S.C. 154(b) by 94 days.

(21) Appl. No.: 15/291,950

(22) Filed: Oct. 12, 2016

(65) Prior Publication Data

US 2017/0119928 A1 May 4, 2017

(30) Foreign Application Priority Data

Nov. 3, 2015 (DE) .................. 10 2015 118 789

(51) Int. Cl.
*A61F 2/24* (2006.01)
*A61L 27/36* (2006.01)
*A61L 27/50* (2006.01)

(52) U.S. Cl.
CPC ........ *A61L 27/3687* (2013.01); *A61F 2/2418* (2013.01); *A61F 2/2427* (2013.01); *A61L 27/3679* (2013.01); *A61L 27/3683* (2013.01); *A61L 27/507* (2013.01); *A61L 2430/20* (2013.01); *A61L 2430/40* (2013.01)

(58) Field of Classification Search
CPC ....................................................... A61F 2/24
See application file for complete search history.

(56) References Cited

U.S. PATENT DOCUMENTS

| | | | |
|---|---|---|---|
| 4,357,274 | A | 11/1982 | Werner |
| 2009/0324684 | A1 | 12/2009 | Atanasoska et al. |
| 2010/0030340 | A1 | 2/2010 | Wolfinbarger, Jr. et al. |
| 2012/0143227 | A1 | 6/2012 | Steckel et al. |
| 2013/0158658 | A1 | 6/2013 | Hayzlett |
| 2015/0282930 | A1 | 8/2015 | Lehenberger et al. |

FOREIGN PATENT DOCUMENTS

| | | |
|---|---|---|
| EP | 2668966 A1 | 12/2013 |
| EP | 2893905 A1 | 7/2015 |
| EP | 2926840 | 10/2015 |
| WO | 1999/66967 A1 | 12/1999 |
| WO | WO2005/024099 A1 | 3/2005 |

OTHER PUBLICATIONS

EP16192568.0 European Search Report dated Mar. 23, 2017.
EP14150896.0 European Search Report dated Aug. 31, 2016.
DE 102015118789.2 German Search Report dated Mar. 14, 2016.

*Primary Examiner* — Matthew W Schall
(74) *Attorney, Agent, or Firm* — Wagenknecht IP Law Group PC

(57) ABSTRACT

A method for preparing tissue, in particular pericardial tissue, in particular for use as a sealing means for a heart valve prosthesis for paravalvular leaks, characterised in that the tissue, in particular pericardial tissue, is decellularized (4), subjected to a cross-linking (6) with a glutaraldehyde-containing solution, and subjected to a shape- and a structure-stabilising step (7, 8, 9). The invention also relates to a heart valve prosthesis.

18 Claims, 2 Drawing Sheets

METHOD FOR REDUCING PARAVALVULAR LEAKS WITH DECELLULARIZED TISSUE

CROSS REFERENCE TO RELATED APPLICATIONS

This invention claims benefit of priority to DE 10 2015 118 789.2, filed Nov. 3, 2015, the entire content of which is herein incorporated by reference in its entirety.

TECHNICAL FIELD

The present invention relates to a method for preparing tissue, in particular pericardial tissue, in particular porcine pericardial tissue, preferably for use as a sealing means to seal a heart valve prosthesis with respect to paravalvular leaks, and to a heart valve prosthesis which contains a biological tissue prepared in this way in the dried state.

BACKGROUND OF THE INVENTION

The invention will be described hereinafter on the basis of the example of a method for preparing tissue for use as a sealing means for a heart valve prosthesis. Although the present invention is particularly suitable for the preparation of tissue of this type, it is not limited to this application.

Methods for preparing biological tissue are known for example from EP 2 832 379 A1 and US 2001/004715 A1.

There are in principle two different types of heart valve prosthesis: mechanical valves, which are produced artificially, usually from graphite coated with pyrolytic carbon; and biological prostheses, often made of pericardium tissue usually originating from animal sources (for example pig or cattle). The heart valve formed from the biological or pericardial tissue is usually secured in a main body (for example a firm plastic framework or a self-expanding stent), and this is implanted at the position of the natural valve. Such heart valve prostheses can be, in particular, what are known as TAVI heart valve prostheses (TAVI stands for transcatheter aortic valve implantation).

A problem with prostheses of this type, in principle, resides in paravalvular leaks, that is to say blood which flows past between the surrounding vascular wall and the outside of the implant.

BRIEF SUMMARY OF THE INVENTION

The object of the present invention is therefore to design a method for preparing tissue, in particular pericardial tissue, and a heart valve prosthesis in such a way that the above-mentioned problem is counteracted.

The object is solved in terms of a method for preparing tissue, in particular pericardial tissue, in particular for use as a sealing means for a heart valve prosthesis for paravalvular leaks and in terms of a device having tissue formed by the methods. Advantageous embodiments of these aspects of the present invention will be described hereinafter.

In principle, different types of tissue, in particular biological tissue, and here tissue from mammals, including humans, can be used in the methods. The tissue can be of xenogenic or allogenic origin. Non-human tissue is initially preferred. In particular, tissues are suitable that can have a high swelling capability after they have been prepared and dried. Here, the tissues are subjected to a lesser extent to a mechanical stress than is the case when used as valve material in a heart valve. Tissue types that do not have a pronounced internal fibre structure, but rather an intrinsic sponge-like or branched structure, can thus also be considered. Here, pericardial tissue, mucosa, and kidney tissue, but also tissue from the lung, stomach or intestine, are preferred for use as material for sealing paravalvular leaks. Furthermore, tissue from pig, sheep, goat, horse, crocodiles, kangaroo, ostrich, and from cattle are preferred. Hereinafter, the focus will be specifically on pericardial tissue. However, a person skilled in the art can see that other tissue types, such as those described above, can also be used.

In one aspect of the invention, a method is provided for preparing tissue, in particular pericardial tissue, preferably for use as a sealing means for sealing a heart valve prosthesis with respect to paravalvular leaks, wherein the tissue is decellularized, is then subjected to cross-linking with a glutaraldehyde-containing solution, is then subjected to a shape- and structure-stabilising step, in which the tissue is exposed to a first solution containing glycerol and is exposed to a second solution containing at least one type of polyethylene glycol, wherein the tissue is dried after the shape- and structure-stabilising step.

During the course of what is known as the decellularization of the tissue, cell membranes, intracellular proteins, cell nuclei and/or other cell components are preferably removed as fully as possible from the tissue in order to obtain an extracellular matrix that is as pure as possible. Cells and cell components remaining in the tissue constitute in particular a possible cause of an undesired calcification of the biological implant material. Here, the decellularization is carried out as gently as possible so that the structure of the extracellular matrix and fibre proteins, for example the collagen fibres or elastin in the extracellular matrix, remain unaffected to the greatest possible extent, whereas on the other hand all cells and cell components contained therein are removed from the tissue.

Within the scope of the solution according to the invention, in contrast to conventional methods, at least one strong decellularization agent is used in a high concentration, which massively changes the tissue structure and makes the pores thereof open. This surprisingly positively improves the swelling behaviour of the tissue treated in accordance with the invention. Suitable decellularization agents are those selected from the group consisting of sodium dodecyl sulphate, deoxycholic acid, Triton X-100, and Tween. In a preferred embodiment the decellularization agent is sodium dodecyl sulphate.

After the decellularization, all cell components are removed from the tissue to the greatest possible extent and the biological material consists exclusively of extracellular matrix. In the case of pericardium tissue the extracellular matrix is formed primarily from collagen fibres. In order to achieve a biological material having the most optimal mechanical properties possible and in order to prevent rejection reactions of the receiving body, the fibre proteins during the cross-linking are preferably cross-linked by means of a suitable cross-linking agent by the incorporation of chemical bonds. The cross-linking agent binds to free amino groups of the fibre proteins and forms chemically stable bonds between the fibre proteins. A biological material which is stable in the long-term and which in addition is no longer identified as biological foreign material is thus produced from the three-dimensionally arranged fibre proteins. The stability and the load-bearing capability of the tissue is significantly increased by the three-dimensional cross-linking or linking of the individual fibre proteins via the cross-linking agent. This is key in particular in the case of use as tissue and sealing means in a heart valve, where the tissue is subjected to a permanent, periodic, mechanical loading.

The drying of the tissue, in particular pericardium tissue, is preferably configured such that a slow and gentle removal of the water in the liquid state from the tissue is ensured. This is advantageously achieved for example by the controlled reduction of the ambient moisture of the tissue in a climate chamber with controlled adjustment of the parameters of the ambient atmosphere of the biological tissue.

In accordance with a particularly preferred embodiment of the method according to the invention, provision is made for the dried tissue to be fastened to a heart valve prosthesis as sealing means or part of a sealing means sealing against paravalvular leaks, wherein the tissue is fastened, preferably sewn, to an expandable or self-expanding main body of the implant, which can be implanted by catheter.

In accordance with a particularly preferred embodiment of the method according to the invention, provision is also made for the dried tissue to be arranged or fixed on an outer side of the heart valve prosthesis so that, in the implanted state, it bears against a tissue (for example vascular wall) surrounding the heart valve prosthesis and, as the tissue is rehydrated, seals a gap between the tissue and the heart valve prosthesis on account of an increase in the thickness of the rehydrated pericardial tissue.

Due to the specific selection and combination of glycerol and polyethylene glycol for the shape- and structure-stabilising step, a purposeful protection of the structure of the tissue, in particular of the biological tissue, is surprisingly attained. With the specific combination of glycerol and polyethylene glycol, and in particular polyethylene glycols having different molecular weights, not only is a microscopic shape stability of the treated biological tissue achieved during the drying, but the microscopic tissue structures are protected and obtained by the stabilisation of the hydrogen bridges. Since the infiltration depth of polyethylene glycol into the biological tissue is dependent on the molecular weight, a stabilising effect is achieved at different tissue depths. In addition, specific protection of the biological tissue to be dried is achieved as a result of the combination. Glycerol and polyethylene glycol penetrate the tissue and stabilize the structure. Polyethylene glycol additionally settles in a concentrated manner on the surface of the tissue and shields it against external influences. Due to the specific use of polyethylene glycol in combination with glycerol, preferably in two solutions, the swelling ability of the treated tissue is obtained as a result of stabilisation of the microscopic tissue structures. This promotes an increase in thickness as the dry tissue treated in accordance with the invention is rehydrated.

In accordance with a preferred embodiment of the method according to the invention, provision is also made for the first solution to contain glycerol and for the second solution to contain polyethylene glycol.

In accordance with a preferred embodiment of the method according to the invention, provision is also made for the tissue to be exposed to a third solution containing polyethylene glycol having a different, preferably greater mean molecular weight compared with the second solution, prior to the drying in the shape- and structure-stabilizing step.

The advantages of the invention are particularly pronounced in this preferred embodiment of the method according to the invention. This embodiment is based on the theory, without being bound hereto, that the infiltration depth of polyethylene glycol in the biological tissue is dependent on the molecular weight. This presumably is dependent on the viscosity, which changes with the molecular weight. The use of a second solution containing polyethylene glycol and of a third solution containing polyethylene glycol with a different, in particular greater mean molecular weight compared with the first solution makes it possible to produce stabilization effects at different tissue depths. In this embodiment of the invention it is possible in particular to obtain and stabilize the microscopic tissue structures accordingly. The use of the third solution also likewise promotes an increase in the thickness during the rehydration of the dry tissue treated in accordance with the invention, in particular pericardial tissue.

In accordance with a preferred embodiment of the method according to the invention, provision is also made for the second solution to contain polyethylene glycol having a mean molecular weight between 100 g/mol and 1,000 g/mol, preferably between 100 g/mol and 290 g/mol, in particular 200 g/mol.

In accordance with a preferred embodiment of the method according to the invention provision is also made for the third solution to contain polyethylene glycol having a mean molecular weight between 200 g/mol and 6,000 g/mol, preferably between 300 g/mol and 600 g/mol, in particular 400 g/mol. Here, the molecular weight of the polyethylene glycol is should be greater than the molecular weight of the polyethylene glycol of the second solution.

In accordance with a preferred embodiment of the method according to the invention provision is also made for the tissue to be exposed to the first, second and/or the third solution for 5 minutes to 12 hours, preferably 15 minutes to 2 hours, preferably for 30 minutes.

An embodiment of the method in which the tissue, in particular pericardial tissue, is first contacted with a first solution containing glycerol, then is contacted with the second solution containing polyethylene glycol, and is then contacted with the third solution containing polyethylene glycol has proven to be particularly preferred. In this embodiment the glycerol of the first solution first penetrates the tissue deeply, the polyethylene glycol of the second solution (for example a solution containing polyethylene glycol having a mean molecular weight of 200 g/mol) penetrates the regions close to the surface, and the polyethylene glycol of the third solution (for example a solution containing polyethylene glycol having a mean molecular weight of 400 g/mol) seals the surface.

Within the scope of this application, the indication % v/v relates to a percentage by volume. Unless specified otherwise in respect of a solution, water is used as a solvent for the solutions herein. 100 ml solution with 5% v/v glutaraldehyde contains, accordingly, 5 ml glutaraldehyde. The indication % w/v relates within the scope of this application to a proportion by weight. 100 ml solution with 0.9% w/v sodium chloride contains, accordingly, 0.9 g sodium chloride.

Furthermore, in accordance with a preferred embodiment of the method according to the invention, provision is made for glycerol to be present in the first solution in a concentration of from 5% w/v to 50% w/v, preferably 20% w/v to 40% w/v.

Furthermore, in accordance with a preferred embodiment of the method according to the invention, provision is made for polyethylene glycol to be present in the second and/or the third solution in a concentration of 5% w/v to 60% w/v, preferably of 20% w/v to 50% w/v.

Furthermore, in accordance with a preferred embodiment of the method according to the invention, provision is made for the tissue, in particular pericardial tissue, to be decellularized in an aqueous decellularization solution containing a decellularization agent as described herein. The decellularization agent can be used here as saturated solution. In a further embodiment an unsaturated decellularization solution is used, wherein the decellularization solution preferably comprises 0.1% w/v to 15% w/v of the decellularization agent, preferably 0.5% w/v to 15% w/v of the decellularization agent, preferably sodium dodecyl sulphate, preferably in 0.9% w/v NaCl or a comparable isotonic aqueous solution. In a further embodiment the decellularization solution contains 2% w/v to 10% w/v of a decellularization agent described herein, preferably sodium dodecyl sulphate. In a further embodiment the decellularization solution contains 7.5% w/v to 12.5% w/v of a decellularization agent described herein, preferably sodium dodecyl sulphate.

In accordance with a preferred embodiment of the method according to the invention, provision is also made for the tissue, in particular pericardial tissue, to be exposed to the decellularization solution over a period of from 12 hours to 48 hours, preferably 24 hours, with slight movement, preferably at a temperature in the range of from 15° C. to 40° C., preferably 37° C.

Furthermore, provision is made in accordance with a preferred embodiment of the method according to the invention for the glutaraldehyde-containing solution to comprise 0.04% v/v to 2% v/v glutaraldehyde, preferably in Dulbecco's phosphate-buffered saline solution (DPBS) without Ca/Mg.

Provision is also made in accordance with a preferred embodiment of the method according to the invention for the tissue, in particular pericardial tissue, to be exposed to the glutaraldehyde-containing solution for 1 to 3 days, preferably 2 days, preferably at 2° C. to 10° C., preferably at 4° C., and wherein the tissue, in particular pericardial tissue, is then exposed to the glutaraldehyde-containing solution for 10 to 14 days, preferably 12 days, preferably at room temperature, which typically lies at temperatures from 20° C. to 25° C., is wherein the glutaraldehyde-containing solution is preferably changed every 1 to 3 days, preferably every 2 days.

Provision is also made in accordance with a preferred embodiment of the method according to the invention that the dried tissue is cut to size and hot-pressed, preferably at a temperature in the range of from 40° C. to 70° C., preferably at 60° C., prior to being fastened to the heart valve prosthesis.

In accordance with a further aspect of the present invention, a heart valve prosthesis is disclosed, comprising a tissue treated in accordance with the invention, in particular pericardial tissue, as described herein, wherein the heart valve prosthesis preferably comprises an artificial heart valve and a sealing means which comprises the tissue, in particular pericardial tissue, or which is formed thereby, and wherein the tissue, in particular pericardial tissue, is fastened, preferably sewn, to an expandable or self-expanding main body of the heart valve prosthesis, which can be implanted by catheter.

The tissue, in particular pericardial tissue, or the sealing means is preferably arranged or fixed to an outer side of the heart valve prosthesis, such that, in the implanted state, it bears against a tissue (for example vascular wall) surrounding the heart valve prosthesis and, as the tissue, in particular pericardial tissue, is rehydrated, seals a gap between the tissue and the heart valve prosthesis on account of an increase in the thickness of the rehydrated pericardial tissue.

The possibility of producing dry biological tissue such that it experiences a significant increase in thickness following rehydration makes it possible to use a tissue of this type for the minimisation of paravalvular leaks in the inflow region of (in particular TAVI) heart valves.

A further aspect of the present invention relates to tissue as described herein which has been treated by a method described herein. Furthermore, decellularized and dried tissue is proposed which is characterised in that the tissue, by means of rehydration, preferably in water or blood, has an increase in thickness by at least 110%, more preferably by at least 130%, more preferably by at least 150%, and more preferably by at least 220% compared to the native untreated tissue. Furthermore, the decellularized and dried tissue has more preferably been cross-linked prior to the rehydration. Furthermore, the decellularized and dried tissue has been hot-pressed prior to the rehydration as described herein. Furthermore, the decellularized and dried tissue has been treated with glycerol and at least one polyethylene glycol, preferably with two polyethylene glycols having different molecular weights as described herein prior to the rehydration. Furthermore, the use of such tissues as sealing material for paravalvular leaks in particular in a heart valve prosthesis is proposed.

A large advantage of the solution according to the invention is the use of biological tissue, for example pericardial tissue, as sealing material for paravalvular leaks, which has considerable advantages with regard to thromboembolic complications and possible biocompatibility problems compared with artificial materials. The resultant mechanical and biocompatible properties of the tissue processed as described are not significantly different apart from the surprisingly found increase in thickness compared with tissues processed in the conventional manner, and therefore do not have any significant disadvantages.

BRIEF DESCRIPTION OF THE DRAWINGS

The invention will be explained in greater detail hereinafter on the basis of exemplary embodiments (see FIG. 1) and a comparison, presented in FIG. 2, between an untreated pericardial tissue and a pericardial tissue treated in accordance with the invention. In the drawings.

DETAILED DESCRIPTION

Example 1

Figure 1:
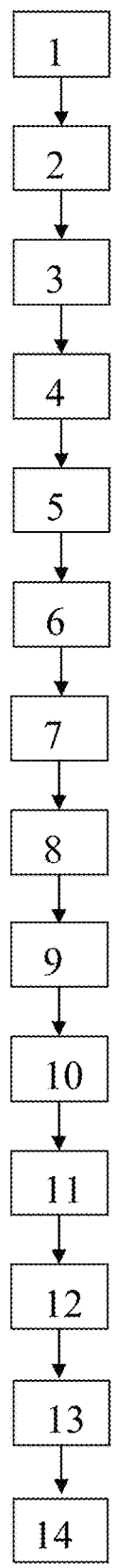
FIG. 1 shows a flow diagram of an embodiment of a method according to the invention.

Example 1 discloses an embodiment of the method according to the invention for preparing porcine pericardial tissue with subsequent drying, illustrated schematically in FIG. 1.

A pericardium is firstly removed fresh from a pig (for example at the slaughterhouse) and is stored for 2 hours at a temperature of 4° C. in a 0.9% w/v NaCl containing penicillin and/or streptomycin (1) [step 1].

In the next step (2), fat and connective tissue are separated in moist state (in 0.9% w/v NaCl) from the pericardial tissue, and the pericardial tissue is cut to size.

The tissue is the rinsed, with slight movement, in 100 ml 0.9% w/v NaCl solution (3).

The pericardial tissue thus obtained is then subjected to a decellularization and subsequent cross-linking.

Figure 2:
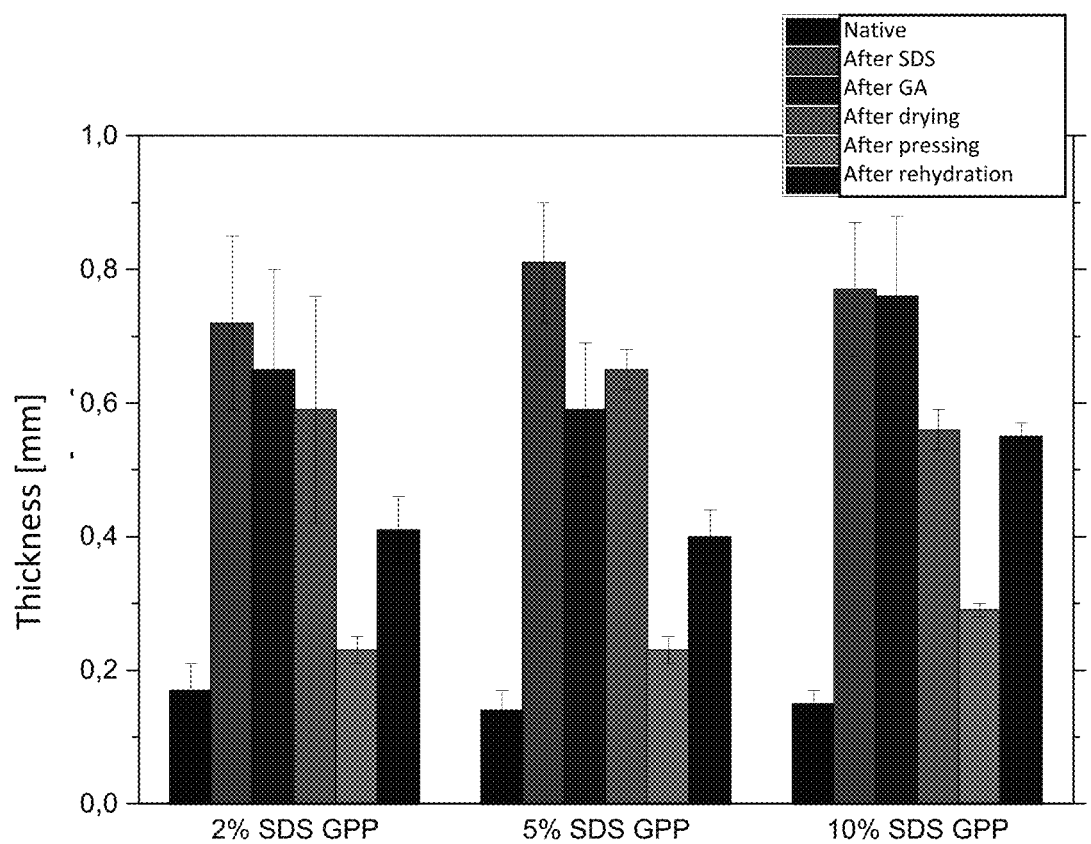
FIG. 2 from left to right: shows the thickness of porcine pericardium in the native state, after subsequent decellularization in 2% w/v, 5% w/v, 10% w/v SDS in 0.9% w/v NaCl, after subsequent cross-linking in 0.65% v/v glutaraldehyde in DPBS without Ca/Mg under slight pretension, after subsequent stabilisation in glycerol 30% w/v, 30 minutes/PEG200 40% w/v, 30 minutes/PEG400, 40% w/v, 30 minutes (GPP, glycerol, PEG200, PEG400) and drying in a climate chamber, after subsequent hot-pressing at 60° C., 10 kg/cm2, 30 minutes, and after subsequent rehydration in 0.9% w/v NaCl, 37° C., 10 minutes.

Here, the pericardial tissue was decellularized with 100 ml 0.5% w/v to 10% w/v SDS (sodium dodecyl sulphate) in 0.9% w/v NaCl for 24 hours at 37° C. with slight movement (4) and then rinsed repeatedly in an aqueous isotonic solution, preferably 0.9% w/v NaCl, with slight movement (5) (see also FIG. 2).

The pericardial tissue was then subjected to a cross-linking (6) with glutaraldehyde, more specifically for 48 hours in 0.04% v/v to 2% v/v glutaraldehyde solution (glutaraldehyde in buffered saline solution at 4° C. (for example DPBS solution, Lonza; DPBS w/o Ca+/Mg+; product number 17-512)), wherein this solution then worked for 12 days at room temperature (typically 20° C. to 25° C.) and was replaced every 48 hours with a similar, fresh solution).

The resultant decellularised and cross-linked pericardial tissue was stabilised in this embodiment of the invention in three steps, wherein the cross-linked pericardial tissue from step (6) was treated for 30 min with slight movement at 37° C. with 20% w/v to 40% w/v glycerol in water (7), then for 30 minutes with slight movement 37° C. with 20% w/v to 50% w/v PEG200 (polyethylene glycol 200) in water (8), and then for 30 minutes with slight movement at 37° C. with 20% w/v to 50% w/v PEG400 (polyethylene glycol 400) in water (9).

The pericardial tissue was then dried, for example in a climate chamber (for example 40° C. and 10% rel. humidity) (10). If the drying is carried out under these conditions for 48 hours, the moisture of the tissue can be reduced from 95% to 10%.

The dry pericardial tissue is cut to size, for example so as to form a sealing means described herein (11).

The dried and cut-to-size shaped pieces are then hot-pressed, for example at 60° C. (12). The hot pressing is typically carried out at a pressure of 2-15 MPa, preferably 5-12 MPa for 5-50 min, preferably for 30 min. Steps (11) and (12) can also be carried out in the reverse order.

The hot-pressed and cut-to-size pericardial tissue is lastly fixed as sealing means to the heart valve prosthesis as described herein (13), wherein the sealing means is designed to seal off paravalvular leaks.

Lastly, the heart valve prosthesis can be loaded onto a catheter and can be sterilised (14).

If the pericardial tissue is now rehydrated at the site of use, its thickness increases significantly and said sealing effect takes hold.

FIG. 2 shows the absolute thicknesses in mm of porcine pericardial tissue at different stages for an exemplary production process. The native tissue with a thickness of less than 0.2 mm increases significantly in thickness by a factor of approximately four as a result of decellularization in the SDS solutions (2% w/v, 5% w/v, 10% w/v). The cross-linking under slight pretension leads to a slight reduction of the thickness with a planar surface. The subsequent stabilization in solutions formed from glycerol/PEG200/PEG400 with subsequent drying in a climate chamber (10% rel. humidity) does not change the thickness significantly. By hot pressing, the thickness of the porcine pericardium pre-treated in this way can be reduced purposefully by a factor of at least two to three. The tissue thickness, after the hot pressing, is again in the range of the native tissue, in particular for the lower SDS concentrations. By means of final rehydration in 0.9% w/v saline solution, the pressed porcine pericardium swells considerably, and the thickness increases by approximately 100%.

In the exemplary embodiment, porcine pericardial tissue, which is used in TAVI valves, is preferably used as starting material. However, in order to seal off paravalvular leaks, the mechanical requirements on the tissue are lower than for valve cusps. As already discussed, the use of other biological tissues without pronounced internal fibre structure can also be implemented, said tissues possibly having an intrinsic sponge-like or branched structure, for example porcine or bovine kidney, stomach or intestinal tissue.

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

What is claimed is:

1. A method for preparing tissue to improve sealing of a vascular prosthesis, the method comprising:
   decellularizing tissue (4);
   subjecting the decellularized tissue to a cross-linking solution (6) comprising glutaraldehyde;
   subjecting the decellularized tissue to a shape- and structure-stabilizing step (7, 8, 9), in which the tissue is exposed to a first solution (7) containing glycerol and is exposed to a second solution (8) containing polyethylene glycol;
   drying the tissue after the shape- and structure-stabilizing step; and
   fastening the tissue to a vascular prosthesis for positioning against an implantation site, thereby improving sealing of the vascular prosthesis against the implantation site;
   wherein the dried tissue is hot-pressed (12).

2. The method according to claim 1, wherein the tissue is fastened to an expandable or self-expanding main body of the vascular prosthesis.

3. The method according to claim 1, wherein the fastened tissue is dried tissue and as the tissue is rehydrated at the site of implantation, the rehydrated tissue seals a gap between the tissue and vascular prosthesis on account of an increase in thickness of the rehydrated tissue.

4. The method according to claim 1, further comprising exposing the tissue to a third solution (9) containing polyethylene glycol having a mean molecular weight different from the second solution, prior to the step of drying (10) the tissue.

5. The method according to claim 4, characterised in that the third solution contains polyethylene glycol having a mean molecular weight between 200 g/mol and 6,000 g/mol.

6. The method according to claim 4, characterised in that the tissue is exposed to the first, second and/or the third solution for 5 minutes to 2 hours.

7. The method according to claim 4, characterised in that the polyethylene glycol is present in the second and/or the third solution in a concentration of from 5% w/v to 60% w/v.

8. The method according to claim 1, characterised in that the glycerol is present in the first solution in a concentration of from 5% w/v to 50% w/v.

9. The method according to claim 1, characterised in that the second solution contains polyethylene glycol having a mean molecular weight between 100 g/mol and 1,000 g/mol.

10. The method according to claim 1, characterised in that the tissue is decellularized (4) in an aqueous decellularization solution containing a decellularization agent, wherein the decellularization solution comprises 0.1% w/v to 15% w/v of the decellularization agent.

11. The method according to claim 10, characterised in that the step of decellularizing the tissue comprises exposing the tissue to a decellularization solution over a period from 12 hours to 48 hours (4).

12. The method according to claim 1, characterised in that the tissue is of xenogenic or allogenic origin.

13. The method according to claim 1, characterised in that the dried tissue, prior to being fastened to the vascular prosthesis, is cut to size (11) and hot-pressed (12).

14. The method according to claim 1, wherein the vascular prosthesis is a heart valve prosthesis.

15. The method according to claim 14, characterised in that the dried tissue, prior to being fastened to the heart valve prosthesis, is cut to size (11) and hot-pressed (12) at a temperature in a range of 40° C. to 70° C.

16. The method according to claim 15, characterised in that the step of decellularizing the tissue comprises exposing the tissue to a decellularization solution over a period from 12 hours to 48 hours (4), and at a temperature in the range of from 15° C. to 40° C.

17. The method according to claim 1, characterised in that the tissue is of xenogenic or allogenic origin, and sought from a member selected from the group consisting of pericardial tissue, mucosa, kidney tissue, and tissue from the lung, stomach or intestine.

18. The method according to claim 1, characterised in that the second solution contains polyethylene glycol having a mean molecular weight of 100 g/mol to 200 g/mol.

\* \* \* \* \*